United States Patent [19]
Roberts

[11] 3,987,559
[45] Oct. 26, 1976

[54] FOOT TREATMENT SHOE AND METHOD OF USING SAME

[76] Inventor: Edith V. Roberts, 2009 S. 19th, Kansas City, Kans. 66106

[22] Filed: Apr. 12, 1976

[21] Appl. No.: 675,700

[52] U.S. Cl. .................................................. 36/95
[51] Int. Cl.² ........................................ A43B 7/30
[58] Field of Search ................ 36/95, 43; 128/582; 12/142 R

[56] References Cited
UNITED STATES PATENTS

| | | | |
|---|---|---|---|
| 611,860 | 10/1898 | Hayward | 36/95 |
| 2,330,398 | 9/1943 | Vass | 36/95 |

*Primary Examiner*—Patrick D. Lawson
*Attorney, Agent, or Firm*—Fishburn, Gold & Litman

[57] ABSTRACT

A foot treatment shoe for use to soften rough skin, calluses, bunions, corns, and the like includes an abrasive surface, such as a layer of fine abrasive material on the interior surface or selected portions of a bottom wall and side walls of the shoe. The shoe includes an upper portion mounted on the lower portion and capable of enclosing a foot therein whereby walking while wearing the shoe is effective to massage the feet within the shoes by means of engagement of the foot with the abrasive material. Use of the shoe includes applying a protective material to the foot prior to placing the shoe on the foot and walking while wearing same.

10 Claims, 3 Drawing Figures

FOOT TREATMENT SHOE AND METHOD OF USING SAME

The present invention relates to a shoe or slipper and more particularly to a shoe or slipper for use to soften rough skin, calluses, corns, bunions, and the like.

Present home treatment methods for rough skin, calluses, corns, bunions, and the like requires extensive time and often leaves the feet tender or sore, or both. For example, use of razor blades in the removal of corns, calluses, or bunions can result in injury to feet or hands. Manual use of sandpaper or the like in smoothing rough skin, calluses, corns, and the like can be extremely tiresome and tedious. Other methods of home treatment of the feet require that the person remain idle while soaking the feet, or the like. The method of the present invention permits activity by the person, such as continuing normal activities during treatment to soften rough skin, calluses, bunions, corns, and the like.

The principal objects of the present invention are: to provide a foot treatment shoe for use to soften rough skin, calluses, corns, bunions, and the like; to provide such a shoe which is comfortable to wear during treatment and which is characterized by not causing the feet to be sore and tender; to provide such a foot treatment shoe which is particularly adapted for home use and is easily cleaned after each use; to provide such a foot treatment shoe having a resilient sole member and a flexible upper portion whereby walking while wearing the shoe effects a gentle massage of the foot by an abrasive surface, such as a layer of fine abrasive material on an interior surface of a bottom wall and a side wall of a lower portion of the shoe; and to provide such a foot treatment shoe which is economical to manufacture, durable in construction, easy to use, and particularly well adapted for the proposed use.

Other objects and advantages of this invention will become apparent from the following description taken in connection with the accompanying drawings wherein are set forth, by way of illustration and example, certain embodiments of this invention.

The drawings constitute a part of the specification and include an exemplary embodiment of the present invention and illustrate various objects and features of the foot treatment shoe and method of using same.

Figure 1:
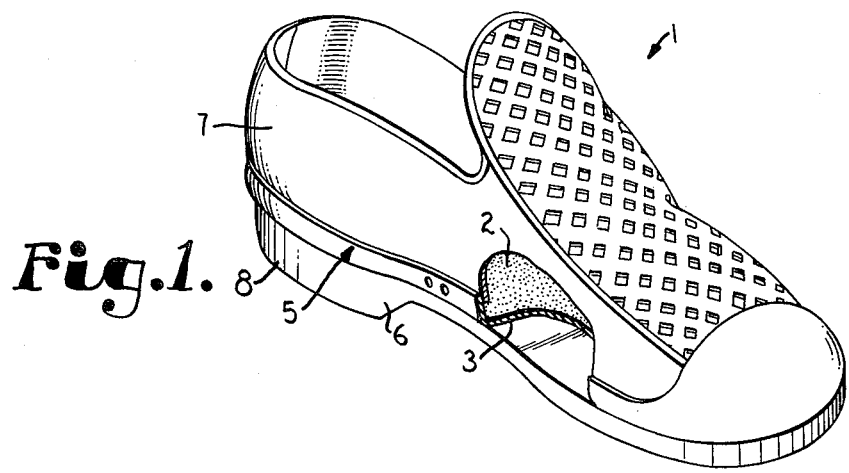
FIG. 1 is a perspective view of a foot treatment shoe embodying features of the present invention.
Figure 2:
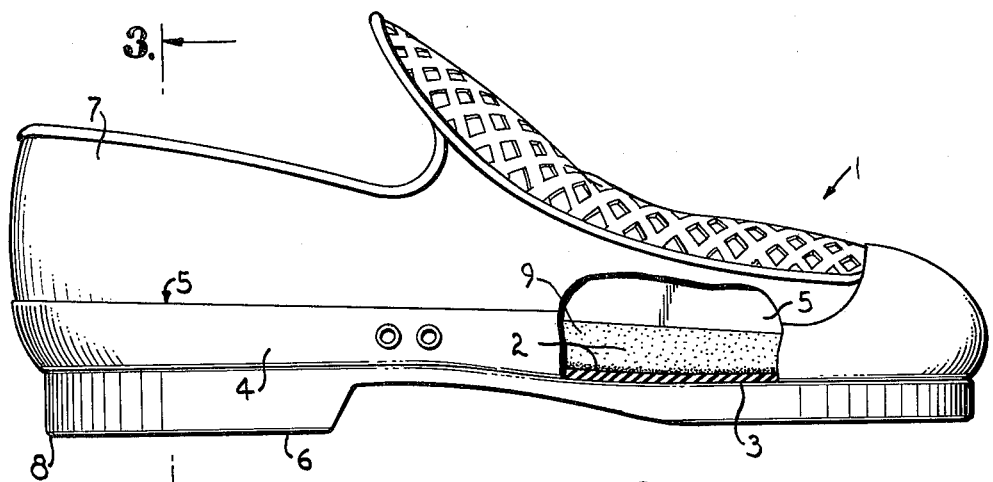
FIG. 2 is a side elevational view of the foot treatment shoe with portions broken away to illustrate a layer of fine abrasive material on an interior surface of the shoe.
Figure 3:
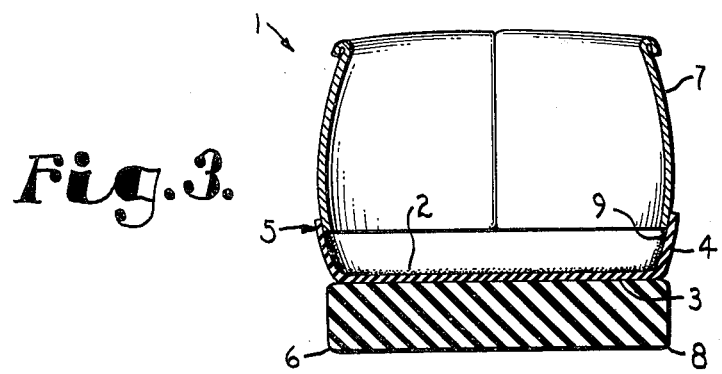
FIG. 3 is a transverse sectional view taken on line 3—3 of FIG. 2.

As required, detailed embodiments of the present invention are disclosed herein. However, it is to be understood that the disclosed embodiments are merely exemplary of the invention which may be embodied in various forms. Therefore, specific structural and functional details disclosed herein are not to be interpreted as limitng but merely as a basis for the claims and as a representative basis for teaching one skilled in the art to variously employ the present invention in virtually any appropriately detailed structure.

Referring more in detail to the drawings:

In the disclosed embodiment of the present invention, the reference numeral 1 designates generally a foot treatment shoe for use to soften rough skin, calluses, bunions, corns, and the like. The foot treatment shoe includes an abrasive surface, such as a layer of fine abrasive material 2 on the interior surface of a shoe or selected portions thereof and particularly a bottom wall 3 and side walls 4 of a lower portion 5 mounted on and extending upwardly from a sole member 6. The shoe 1 includes an upper portion 7 mounted on the lower portion 5 and capable of enclosing a foot therein whereby walking while wearing the shoe 1 is effective to massage the feet within the shoes 1 by means of engagement of the foot with the abrasive material 2. Use of the shoe 1 includes applying a protective material to the foot prior to placing the shoe 1 on the foot and walking while wearing same.

The sole member 6 may be formed of any suitable flexible material which is durable and may be used in any suitable area and particularly as a house shoe or slipper. The sole member 6 is preferably formed of resilient or yieldable material so that the shoe 1 is comfortable to wear in standing or walking and while wearing the shoe 1 the structure thereof effects a gentle massage of the foot therein. The sole member 6 may have a heel portion 8 so that wearing the shoe 1 has the feel of wearing a conventional shoe. The heel portion 8 is preferably also formed of resilient material thereby cooperating with the sole member 6 in effecting massage of the foot therein.

The lower portion 5 is suitably secured to the upper surface of the sole member 6, as by stitching, glue, adhesive, or the like. The lower portion 5 has the bottom wall 3 thereof secured to the sole member 6 and the side wall 4 extends upwardly from a peripheral edge portion of the bottom wall 3. The side wall 4 has a height substantially equal to or slightly greater than the thickness of a foot to be received in the foot treatment shoe 1 and the side wall 4 has an interior foot engaging surface 9. The lower portion 5 is preferably formed of a flexible material so that the side wall 4 thereof cooperates with the sole member 6 in effecting massage of the foot within the shoe 1.

The upper portion 7 is mounted on the lower portion 5 and is capable of enclosing the foot therein. The upper portion 7 is also preferably formed of flexible material to cooperate with the sole member 6 and the lower portion 5 in effecting massage of the foot within the shoe 1. The upper portion 7 may have a porous or open portion, such as a mesh or the like, to permit air circulation within the shoe 1. The upper portion 7 preferably has the upper edges thereof finished to provide a durable edge, such as being folded and stitched substantially parallel with the upper edge.

The abrasive material 2 defining the abrasive surface on the interior surface 9 of the bottom wall 3 and side wall 4 of the lower portion 5 or selected portions thereof is engageable with respective portions of the foot within the shoe 1. The abrasive material 2 is suitably secured on the interior surface 9 of the lower portion 5 in any suitable manner, such as in a layer of adhesive, glue, or the like applied to the interior surface 9 of the bottom wall 3 and the side wall 4 of the lower portion 5. The abrasive material 2 may be any suitable fine grit material, such as very fine sand, pumice, or the like applied to the surface 9 or a surface texture or the like on the surface 9, which when gently moved over respective surfaces of a foot within the shoe smooths rough skin, calluses, bunions, corns, and the like.

The method of using the foot treatment shoe 1 in treating feet to soften rough feet, calluses, bunions, corns, and the like, includes applying a protective material to the feet to coat same therewith. Suitable protective materials include oils, skin lotions, talcum powder, and the like to retard abrasion and cause the grit or abrasive material to provide a massage of the foot. After coating at least the sole and sides of the feet, a respective foot treatment shoe 1 is placed on each of the feet so that the layer or portions of abrasive material 2 therein is engageable with the respective feet.

Walking while wearing the foot treatment shoe 1 effects a massage of the feet due to the resilient action of the sole member 6 and the flexible action of the side wall 4 and the upper portion 7. Engagement of the sides and sole of the feet with the layer of abrasive material 2 smooths rough skin, calluses, corns, bunions, and the like. The protective liquid or powder smooths the feet and cooperates with the adhesive material 2 in softening the feet while within the foot treatment shoe 1.

It is to be understood that while I have illustrated and described one form of my invention, it is not to be limited to the specific form or arrangement of parts herein described and shown.

What I claim and desire to secure by Letters Patent is:

1. A foot treatment shoe comprising:
   a. a sole member and a side wall extending upwardly therefrom and defining an interior bottom wall and side wall having interior foot engaging surfaces capable of enclosing a foot therein; and
   b. a fine abrasive surface on selected interior foot engaging surfaces of the bottom wall and the side wall and engageable with the foot therein.

2. A foot treatment shoe as set forth in claim 1 wherein said sole member and said side wall portion are each formed of flexible material.

3. A foot treatment shoe as set forth in claim 1 wherein said abrasive surface is formed of fine abrasive material.

4. A foot treatment shoe comprising:
   a. a sole member;
   b. a foot enclosing portion mounted on said sole member and having a bottom wall and a side wall defining interior foot engaging surfaces; and
   c. fine abrasive material on selected interior foot engaging surfaces of the bottom wall and side wall of said foot enclosing portion and engageable with the foot therein.

5. A foot treatment shoe as set forth in claim 4 wherein said foot enclosing portion includes:
   a. a lower portion mounted on sole member and having a bottom wall and a side wall extending upwardly therefrom; and
   b. an upper portion mounted on said wall of said lower portion.

6. A foot treatment shoe as set forth in claim 5 wherein said lower portion and said upper portion are formed of flexible material whereby said lower portion and said upper portion cooperate to massage the foot within the shoe.

7. A foot treatment shoe as set forth in claim 6 wherein said abrasive material is pumice.

8. A method of treating feet to soften rough feet and calluses and bunions and including the steps of:
   a. applying a protective material to the feet to coat same therewith;
   b. placing the feet in respective shoes each having a resilient sole member and a flexible lower portion mounted on the sole member and having a layer of fine abrasive material on selected interior surfaces of the lower portion, said abrasive material being positioned to engage at least a sole portion and a side portion of the respective foot; and
   c. walking while wearing the shoes with the abrasive material on the interior surface thereof to thereby massage the feet within said shoes.

9. A method of treating feet as set forth in claim 8 wherein said applying a protective material to the feet includes applying a liquid to the sole portion and a side portion of each of the feet.

10. A method of treating feet as set forth in claim 8 wherein said applying a protective material to the feet includes applying a powder to the sole portion and a side portion of each of the feet.

* * * * *